United States Patent
Touati et al.

(10) Patent No.: US 7,853,045 B2
(45) Date of Patent: Dec. 14, 2010

(54) GEOSTATISTICAL ANALYSIS AND CLASSIFICATION OF CORE DATA

(75) Inventors: Mustafa Touati, Dhahran Hills (SA); Shameem Siddiqui, Lubbock, TX (US); Taha Mostafa Hamed Okasha, Alkhobar (SA)

(73) Assignee: Saudi Arabian Oil Company, Dhahran (SA)

( * ) Notice: Subject to any disclaimer, the term of this patent is extended or adjusted under 35 U.S.C. 154(b) by 655 days.

(21) Appl. No.: 11/982,006

(22) Filed: Oct. 31, 2007

(65) Prior Publication Data

US 2009/0110242 A1   Apr. 30, 2009

(51) Int. Cl.
*G06K 9/00* (2006.01)

(52) U.S. Cl. .............................. 382/109; 702/6; 702/9; 702/11; 702/13

(58) Field of Classification Search ................. 382/109, 382/168, 170; 702/6, 9, 11, 13; 703/10
See application file for complete search history.

(56) References Cited

U.S. PATENT DOCUMENTS

| | | | |
|---|---|---|---|
| 5,430,291 A * | 7/1995 | Pepin et al. ................. | 250/255 |
| 5,675,147 A | 10/1997 | Ekstrom et al. | |
| 5,848,379 A | 12/1998 | Bishop | |
| 6,178,807 B1 * | 1/2001 | Baldwin et al. ................. | 73/38 |
| 6,195,092 B1 | 2/2001 | Dhond et al. | |
| 6,370,547 B1 | 4/2002 | Eftink | |
| 6,430,547 B1 | 8/2002 | Busche et al. | |
| 6,480,790 B1 | 11/2002 | Calvert et al. | |
| 6,816,787 B2 * | 11/2004 | Ramamoorthy et al. ......... | 702/7 |
| 6,826,483 B1 | 11/2004 | Anderson et al. | |
| 6,829,570 B1 | 12/2004 | Thambynayagam et al. | |
| 7,133,779 B2 * | 11/2006 | Tilke et al. ...................... | 702/9 |
| 7,277,795 B2 * | 10/2007 | Boitnott ......................... | 702/6 |
| 2002/0042702 A1 | 4/2002 | Calvert et al. | |
| 2003/0115029 A1 | 6/2003 | Calvert et al. | |
| 2004/0098200 A1 | 5/2004 | Wentland et al. | |
| 2004/0122634 A1 | 6/2004 | Calvert et al. | |
| 2004/0215428 A1 | 10/2004 | Bras et al. | |
| 2004/0225441 A1 | 11/2004 | Tilke et al. | |
| 2005/0015204 A1 | 1/2005 | Xue | |
| 2005/0116709 A1 | 6/2005 | Proett et al. | |
| 2005/0149360 A1 | 7/2005 | Galperin | |
| 2005/0240349 A1 | 10/2005 | Goswami et al. | |
| 2005/0256643 A1 | 11/2005 | Boitnott | |
| 2006/0136135 A1 * | 6/2006 | Little et al. .................... | 702/13 |

OTHER PUBLICATIONS

Shine, "Compression and Analysis of Very Large IMagery Data Sets Using Spatial Statistics," http://www.galaxy.gmu.edu/interface/I01/I2001Proceedings/JShine/JShine-Paper.pdf.

* cited by examiner

*Primary Examiner*—John B Strege
(74) *Attorney, Agent, or Firm*—Abelman, Frayne & Schwab

(57) ABSTRACT

A novel database and method of classifying and searchably retrieving measurement data derived from a plurality of rock core and plug sample images that are analyzed to define their principal geostatistical attributes and characteristics, with the resulting analytical data being retrievably stored in a database, the method including calculating spatial variability of images, such as CT scan images, porosity images and other types of available images, quantifying the main image characteristics utilizing multi-azimuth variograms and simplified pattern recognition based on the histogram and variography analysis to thereby provide a means to correlate data from various geographical regions or fields by analyzing data which has the same variographic parameters.

15 Claims, 5 Drawing Sheets

GEOSTATISTICAL ANALYSIS AND CLASSIFICATION OF CORE DATA

FIELD OF THE INVENTION

This invention relates to the analysis and storage in a database of the characteristics of geological core and core plug samples that are retrievable based upon the correlation of the characteristics of the data.

BACKGROUND OF THE INVENTION

The recovery, indexing and storage of core samples is routinely undertaken in connection with a wide variety of scientific and commercial activities including the study of the earth's geology, exploration for recovery of hydrocarbons and the mining of other minerals, and the analysis of construction sites, among many others. In the field of petroleum exploration and recovery, oil companies, oil field service companies, mining and environmental companies and agencies commonly deal with core samples.

The cores are typically cataloged and stored at a laboratory site and are individually subjected to a variety of tests and measurements by scientists and technicians. The processing known as "Routine Core Analysis" (RCAL) includes measurement of porosity, grain density, horizontal permeability, fluid saturation, and a lithologic description. Routine core analysis can also include a core gamma log and measurements of vertical permeability, which can be taken at room temperature and either at ambient pressure, formation confining pressure, or both. Routine core analysis is to be distinguished from "Special Core Analysis" (SCAL) in which relative-permeability and capillary pressure data are obtained, usually for the purpose of performing reservoir simulation analysis.

Data analysis and simulation methods have been developed to enable the user to allocate selected relative-permeability and capillary pressure curves to appropriate blocks in the simulation grid automatically by applying pre-determined criteria. Three-dimensional visualization capabilities provide a rapid and effective way of confirming and comparing data allocations.

In accordance with the methods of the prior art, a core is removed from a storage facility by a laboratory technician and is subjected to testing to provide RCAL and SCAL measurements and these measurements are entered into a database. In response to an inquiry for relevant RCAL and/or SCAL data, a technician views stored images, e.g., on a monitor linked to the database. One or more communications must then be exchanged with an expert in the lab and/or geologists for a description of the sample. A further common step is to return to the core storage facility to obtain the core layout and to then make a comparison between cores from two or more other wells or fields.

When considering the field of hydrocarbon exploration and production, the steps of subjecting the cores or core plugs to analysis in order to obtain values for the various characteristics mentioned above and storing them is solely for the purpose of having the data available in a form that can be used by other engineers and scientists who are studying the geological, petrophysical and geophysical information for a variety of purposes. The data collected as described above is stored in hard and soft databases.

Core data provides a highly reliable source of information about reservoir characteristics and can be used for significant geological interpretations. The prior art has developed the technology to permit users to view images of more than one database, e.g., of whole cores and of slabs, at their desktop computer monitors. However, data are typically indexed by well name, depth and formation. Core and plug data are conventionally stored as images. Even when optimized, the prior art procedures for completing conventional and special core analyses and thin section analysis can be time-consuming.

Catalogs of thin sections of rock have also been constructed. However, at present the user must undertake a comparative visual search of the catalog for each new thin section image to establish similarity. In other words, images must be browsed, one-by-one, in order to make the appropriate match. Users sometime experience difficulty in making the appropriate correlations.

It is also known to prepare variograms and histograms based on data collected from samples in order to further characterize the reservoir samples. Variogram models are also known that are based on data obtained empirically, or from actual tests performed on core samples.

Although the numerous measurements that have been customarily and routinely obtained are useful, alternative means for characterizing and storing data in a form that is rapidly retrievable and which can be correlated would be desirable. It would also be desirable to provide an improved method and system to enable users to more quickly and accurately locate, identify and correlate relevant images from existing databases.

It is therefore one object of the present invention to provide a method and apparatus for the efficient classification and correlation of cores and plugs utilizing a novel form of characterizing data.

Another object of the invention is to provide such an apparatus and method that is efficient in terms of time and the physical effort required to assemble and store the data in retrievable form and that can be easily correlated.

It is a further object of the present invention to provide an improved method and system for matching and retrieving core images and computerized tomography (CT) images.

Yet another object of the invention is to provide a system and method to store and retrieve image data based on the specific properties of cores and plugs and to reduce the time required to obtain the desired data and images.

SUMMARY OF THE INVENTION

The above objects and other advantages are achieved by the present invention in which core and plug sample images are analyzed to define their principal geostatistical attributes and the resulting analytical data is retrievably stored based upon these attributes. Specifically, core and plug data are analyzed by calculating the spatial variability of images, such as CT scan images, porosity images and other types of available images, and quantifying the main image characteristics utilizing multi-azimuth variograms to thereby provide a means to correlate data from various geographical regions or fields by sorting, collecting and analyzing data which has the same variographic parameters. This methodology utilizes simplified pattern recognition based on the histogram and variography analysis.

In accordance with the present invention, a new database is developed in which histograms and variograms for the core samples, slabs and thin slices are stored in a searchable format for retrieval. The images are classified using variograms and the characterizing parameters are stored in a database for subsequent correlation of CT scan images from various geographical fields and reservoirs. The parameters that are sorted and classified in the database contain all the spatial variability present in the images.

The variogram has proven to be a useful tool in analyzing core and CT scan images. The stored parameters of the variogram can include type of variability, range, sill and anisotropies. Use of this searchable database results in significant time savings in classifying types of heterogeneities and locating data from wells and intervals with the same core properties. The system and method of the invention thus provides a new quantitative tool for comparison of core images and CT scans.

The method and apparatus of the invention thus eliminates the need for an examination of the soft database on an image-by-image basis, and utilizes a method that has been proven to be useful in other macro-scale applications. The application of geostatistical techniques on a macro-scale have been successfully employed in reservoir characterization and geologic modeling using simulations. The technique also includes equiprobable realizations for similar geostatistical properties.

As will be apparent to those of ordinary skill in the art, the elimination or reduction in the need for conducting a physical examination of a specific core or plug sample or the examination of the database image-by-image will result in a substantial savings of personnel time, effort and therefore expense.

In accordance with the method of the invention, core imaging includes two- and three-dimensional images obtained by CT scans of the cores, the analysis of the images utilizing geostatistical variography and the determination of key parameters and the entry into data storage of the key image parameters and the associated image(s). Utilizing the new database prepared in accordance with the invention, queries can be made on the basis of image parameters and comparisons of data that have the same image properties can be undertaken with information stored in the database. The invention thus provides the advantage of prompt retrieval of data using spatial variability parameters that are stored in the database. This allows quantification of the main properties of the image, a rapid retrieval of data and also a correlation of data from the same or different reservoirs, formations, and fields. Not only does the method and apparatus of the invention result in the savings of personnel time, effort and costs, it also produces a better understanding of the characteristics of the reservoir as derived from the data correlations.

It has been found that CT scan slices that show Gaussian variables can produce the same histograms, but will exhibit different spatial variability. Thus, in some circumstances, the use of histograms alone will not be sufficient to characterize an image. Where the histograms are similar, geostatistics can be utilized in accordance with the method of the invention to analyze the spatial variability of the core images. Using the method of the invention, it has been found that geostatistical simulations having the same histograms are differentiated by variograms representing different types of spatial variability. In this regard, the core images can be derived from a CT scan or can be other types of images, e.g., density, porosity and NMR images.

The physical database corresponds to the stored collection of core samples, plugs and cuttings, each of which can be retrieved and physically handled, examined and tested in the conventional manner to obtain new or additional data. The physical database is used to create the so-called "soft" database of images that are indexed by geographical characteristics and the identification of the physical sample from which they were derived. A typical search in the soft database can be based on the well, sample identification and depth.

The variograms are created automatically from the image using available software. An automatic variogram fitting identifies the geostatistical parameters for that image. These parameters can include the anisotropy angles, the sill (or variance), the range or correlation length, and the type of variogram, i.e., exponential, spherical or Gaussian. These extracted parameters summarize the spatial variability in the image of the rock. This information is entered into the database for each rock sample where it is stored and available for subsequent correlation and retrieval.

The experimental variogram is constructed from the data obtained from the core samples. A model, or theoretical, variogram is an analytical function which is constructed to fit the experimental variogram. The model variogram is a simplified version of the experimental variogram and is constructed as follows:

a. for each given lag distance, the number of points in the data set that have the same lag distance is determined:

b. the number of pairs are counted and for all of the pairs counted, the quadratic difference between the value at each point is calculated; and c. the quadratic differences for each lag distance is summed and divided by the factor of two times the number of pairs counted in step(b).

The histograms are constructed as follows:

a. the minimum and the maximum of the data set are calculated;

b. the number of bins for which the histogram will be calculated is defined; and c. for each bin, the number of data falling in it are calculated, along with the percentage of data falling into each such bin.

The parameters such as minimum, maximum, average and standard deviation, and the type of variogram, the sill and the range are calculated and are stored in the database. All of the properties calculated for each image are saved to storage. In a preferred embodiment of the invention, image processing of large numbers of samples is done in batch mode during weekends or holidays.

BRIEF DESCRIPTION OF THE DRAWINGS

The invention will be described in further detail below and with reference to the attached drawings in which like or similar elements are referred to by the same number, and where.

DETAILED DESCRIPTION OF PREFERRED EMBODIMENTS

The method of the invention is included in the stepwise procedure that will be broadly described with reference to the flow chart of FIG. 1. The core samples are obtained and logged into the core storage facility in the customary manner which generally includes assigning a unique index identifier which corresponds to a location in the storage facility and the data relating to the geographical area or field, the name or number of the well, and the depth from which the core was extracted. The core is then cut to provide cross sections and/or longitudinal sections, and images are prepared. The images are initially stored in a general purpose database, such as that sold by Oracle. Images are then exported into a specialized geostatistical software package. From these images, data analysis is performed to extract image characteristics. For example, histogram analysis and histogram modeling is performed to find maxima and minima, and other parameters, and to sort the data into bins. Three-dimensional (3-D) variogram analysis and modeling is also performed in which the main axis of anisotrophy is determined. Thereafter, the variogram is calculated in both directions to obtain the main parameters, e.g., nugget, variogram type, range 1, range 2, sill 1 and sill 2. In this regard, reference is made to FIG. 2 which provides an illustration of the results of the CT imaging of core plug cross sections.

Figure 1:
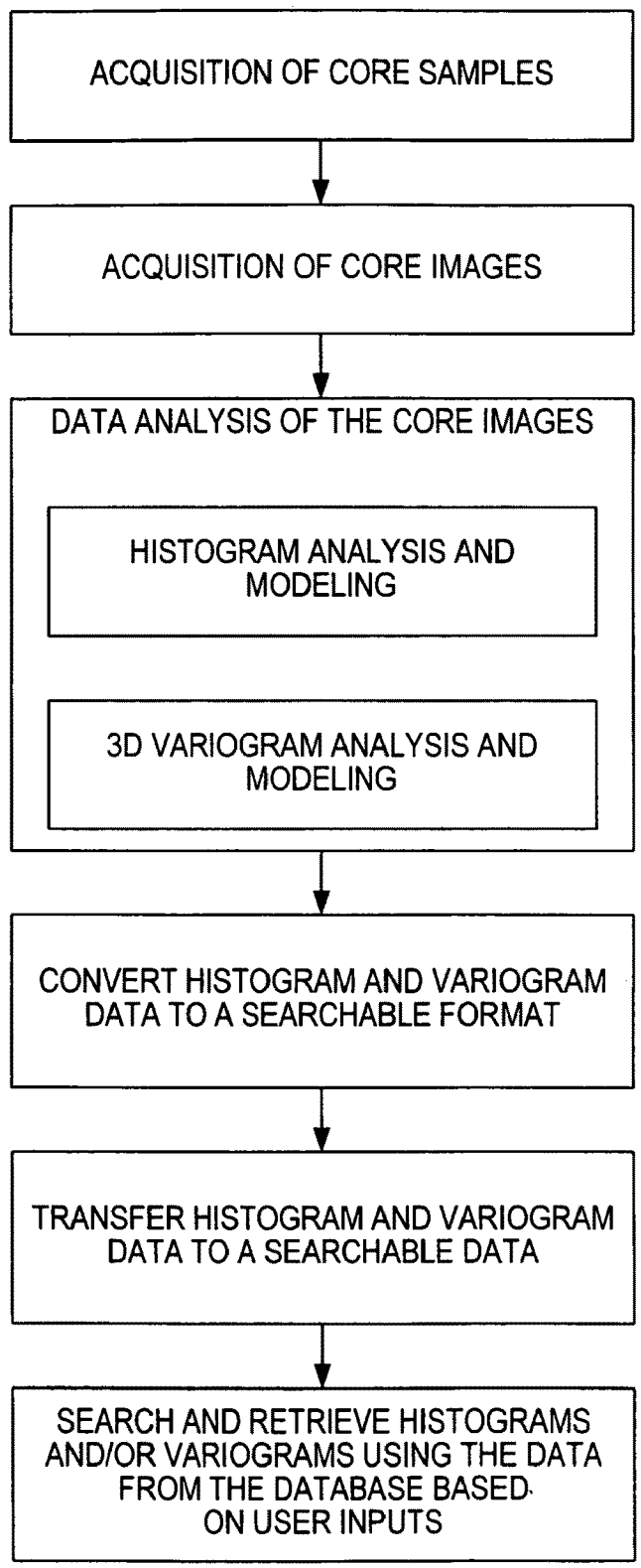
FIG. 1 is a flow chart illustrating a preferred embodiment of the method of the present invention.
Figure 2:
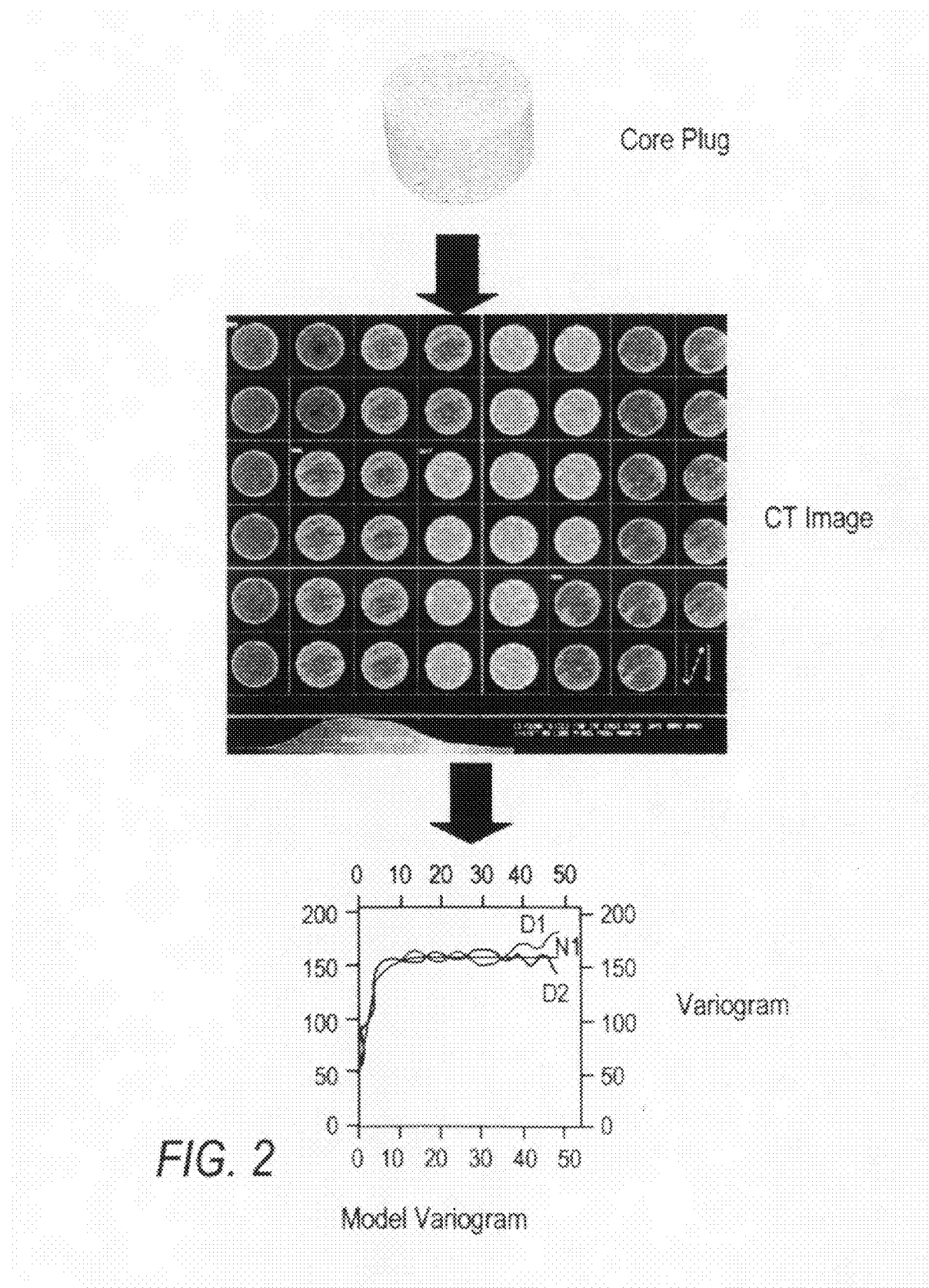
FIG. 2 is a schematic illustration of the method of FIG. 1.

With continuing reference to FIG. 1, in the 3D variogram analysis and modeling step a three-dimensional variogram is constructed from the CT image data and the data derived from the variogram is converted into a searchable format. Similarly, the histogram data is converted into a searchable format. Thereafter, the variogram and histogram data are transferred to the database where they are stored in a searchable and retrievable form. This data can then be searched and retrieved in response to user inputs, such as queries posed by other engineering and scientific groups for the purpose of determining correlations with various reservoir parameters. In a preferred embodiment, the software includes a program for the construction of the corresponding variograms and histograms.

Figure 3:
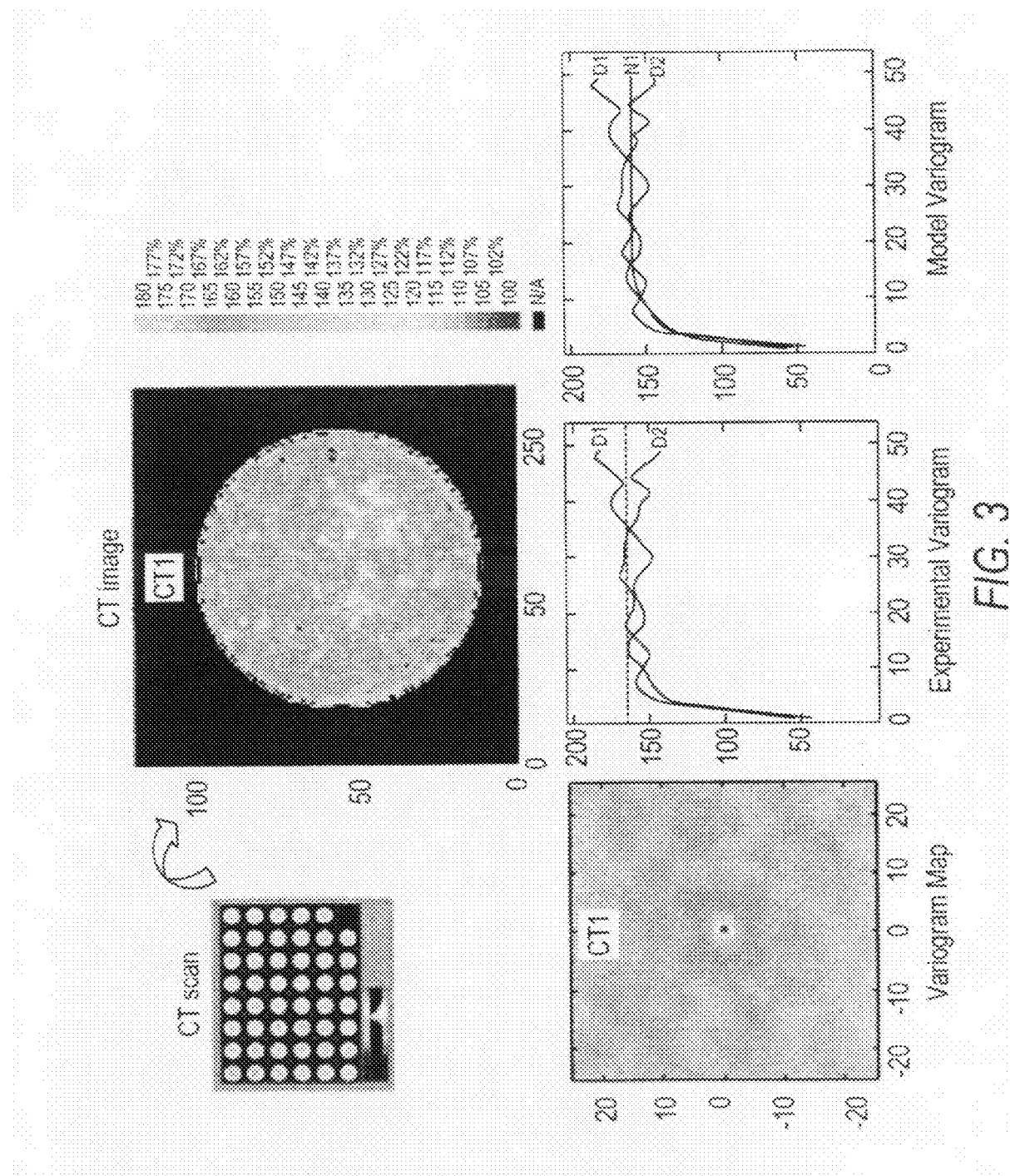
FIG. 3 is a schematic illustration of further embodiment of the method and system of the invention with comparative experimental and model variograms.

Referring now to FIG. 3, there is illustrated a farther step in the method of the invention which includes the preparation of the experimental variogram based upon the variogram map and then its corresponding simplified model variogram to which it has been fitted. The experimental variogram is constructed as follows:

1. for each given lag distance, count the number of points in the data set that have this same lag distance;
2. for all the pairs counted, calculate the quadratric difference between the value at each point; and
3. calculate a summation for the quadratic differences for each lag distance and divide it by the factor 2*(number of pairs)

Figure 4:
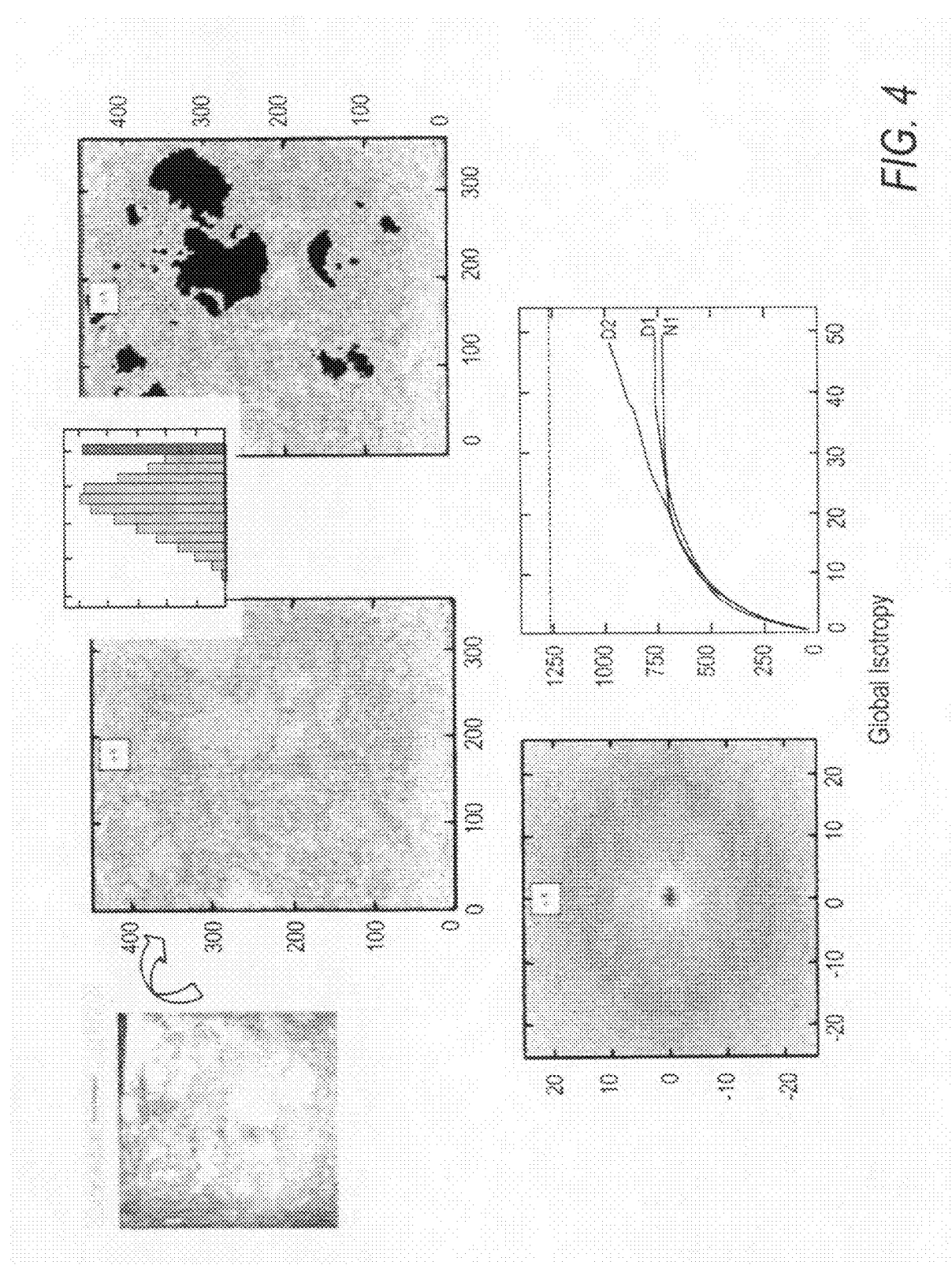
FIG. 4 is a schematic illustration of another embodiment of the method applied to isotropy images with a representative histogram and corresponding variogram.

A further representation of the method of the invention is schematically illustrated in FIG. 4. In the upper left hand side, an image of the rock sample is obtained and then transferred to a geostatistics software processing package. Thereafter, the histogram of the images is constructed and is represented in the form of a vertical bar graph. In the sample illustrated, the histogram is Gaussian in its distribution, with the exception of the outlier which appears to the extreme right of the graph. In the practice of the invention, outliers are eliminated since they are deemed to not accurately represent the slab images.

A variogram map is also constructed for the complete image. It represents the variability of the variogram in each direction. In the center is a variogram of 0 distance; further from the center, is a variogram of a given distance and direction. This variogram map appears to be substantially isotropic, since the iso-values appear to be circular in shape. The lower right illustration is the variogram in the principal directions of zero and 90 degrees. The variogram has been fitted to a model variogram. The parameters of the model variogram are the properties of the rock sample that are stored in the database.

Figure 5:
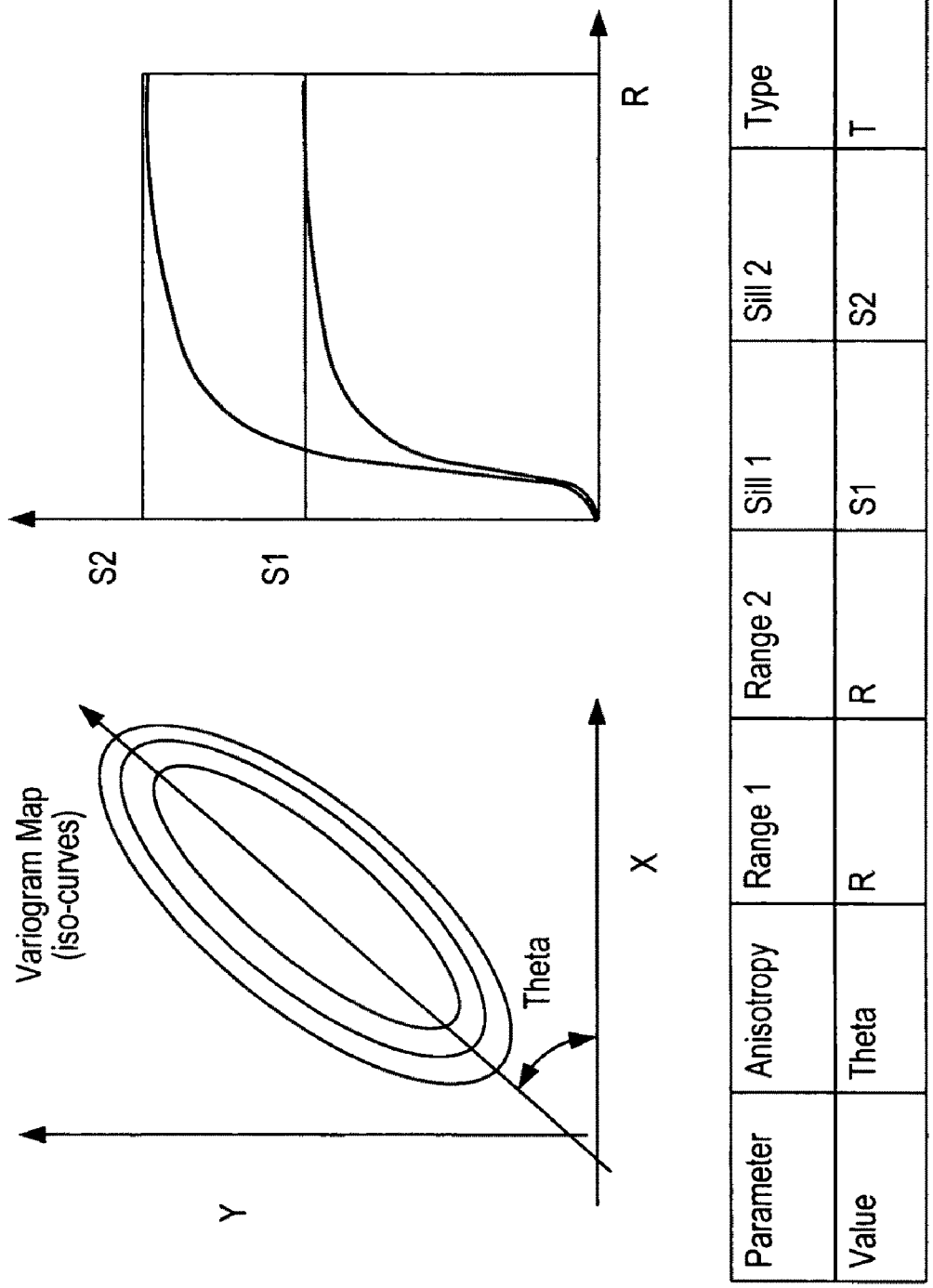
FIG. 5 is a schematic illustration of a variogram map and associated graphic and tabular data displays.

Referring now to the illustrations of FIG. 5, to the left there is shown a two-dimensional variogram map and representative iso-curves developed from the CT scanning of a rock sample. In this instance, the variogram map is elliptical and there are two principal axes of anisotropy. The angle theta is the first principal axis of the ellipse and the angle theta plus 90 degrees is the angle of the second axis of anistrophy. In the graphical depiction to the right, the variograms are shown along the two principal axes of anisotropy. They have different Sills and different ranges; however, for the purposes of this simplified illustration of FIG. 5, they are shown having a similar range. The plots of actual experimental data would typically show differences in range.

The tabular data below the graphs of FIG. 5 summarizes the characteristics of the variogram for this particular sample, which includes the anisotropy, angle theta, the sills, the ranges and the type of the variogram, e.g., "T". As will be understood by those of ordinary skill in the art, variogram can also be of the Gaussian or spherical type.

The invention has been described in detail above and with reference to the attached figures and illustrative examples. Other variations and modifications will occur to those of ordinary skill in the art and the scope of the invention is to be determined with reference to the claims that follow.

We claim:

1. A method of classifying and retrieving measurement data derived from a plurality of rock core and/or plug samples comprising:
   a. scanning sections prepared from each sample at predetermined intervals to provide a plurality of images;
   b. calculating the spatial variability of measurements of at least the main characteristics of the images prepared from each of the samples to provide at least one variographic parameter for each of the characteristics for each of the samples;
   c. entering information into a database that includes a unique sample identifier for each of the plurality of samples and the at least one variographic parameter calculated in step (b) in association with the sample identifier;
   d. sorting and retrieving data corresponding to the main image characteristics based on at least one of the variographic parameters.

2. The method of claim 1, wherein the scanning includes one or more of CT scanning, porosity, horizontal and vertical permeability, grain density, fluid saturation and gamma log density to produce the images.

3. The method of claim 2 which further includes relative-permeability and/or capillary pressure data.

4. The method of claim 1 in which the images are CT scans and the characteristics measured include one or more of spherical, Gaussian and exponential values, the Sill value, the azimuth in two or three dimensions, and anisotropies.

5. The method of claim 1 in which the information entered in the database includes a retrievable image of at least a portion of the sample.

6. The method of claim 5 in which the image corresponds to a scanned section of the sample.

7. The method of claim 1 in which the database includes information from samples obtained from the same or a plurality of wells.

8. The method of claim 1 in which data retrieved is displayed on a monitor.

9. The method of claim 1 in which the data retrieved is displayed graphically.

10. The method of claim 9 in which the data is also displayed in tabular form.

11. The method of claim 1 in which the main image characteristic for a sample is its anisotropy and the display is a variogram map.

12. A non-transitory computer readable medium storing a database for geophysical information that corresponds to a plurality of rock core samples, the database comprising:
   a. a unique sample identifier;
   b. data representing one or more variographic parameters corresponding to predetermined characteristics derived from CT scans prepared from each of the plurality of the core samples; and
   c. input and output means for retrievably storing the data based on at least one of the variographic parameters.

13. The database of claim 12 in which the characteristics include porosity, horizontal and vertical permeability, grain density, fluid saturation and gamma log density.

14. The database of claim 12 which also includes data representing histograms prepared for each of the plurality of rock core samples.

15. The method of claim 1 which includes entering into the database for storage data selected from minimum, maximum and standard deviation, and the type of variogram, the sill and the range as calculated for each sample.

* * * * *